United States Patent
Custelcean et al.

(10) Patent No.: US 9,260,326 B2
(45) Date of Patent: Feb. 16, 2016

(54) SELECTIVE OXOANION SEPARATION USING A TRIPODAL LIGAND

(75) Inventors: Radu Custelcean, Knoxville, TN (US); Bruce A. Moyer, Oak Ridge, TN (US); Arbin Rajbanshi, Knoxville, TN (US)

(73) Assignee: UT-BATTELLE, LLC, Oak Ridge, TN (US)

(*) Notice: Subject to any disclaimer, the term of this patent is extended or adjusted under 35 U.S.C. 154(b) by 793 days.

(21) Appl. No.: 13/485,118

(22) Filed: May 31, 2012

(65) Prior Publication Data

US 2013/0319950 A1  Dec. 5, 2013

(51) Int. Cl.
 *C07D 213/75* (2006.01)
 *C02F 1/52* (2006.01)
 *C02F 101/00* (2006.01)
 *G21F 9/12* (2006.01)
 *C02F 101/10* (2006.01)
 *C02F 1/58* (2006.01)

(52) U.S. Cl.
 CPC ... *C02F 1/52* (2013.01); *C02F 1/58* (2013.01); *C07D 213/75* (2013.01); *G21F 9/12* (2013.01); *C02F 2101/006* (2013.01); *C02F 2101/101* (2013.01)

(58) Field of Classification Search
 CPC ... C07D 213/75; C02F 1/52; C02F 2101/006; C02F 2101/101; C02F 1/58; G21F 9/12
 See application file for complete search history.

(56) References Cited

PUBLICATIONS

Byrne P, Lloyd GO, Anderson KM, Clarke N, Steed JW. Anion hydrogen bond effects in the formation of planar or quintuple helical coordination polymers. ChemComm 2008 3720-3722.*

Ballester P., "Anion Binding in Covalent and Self-Assembled Molecular Capsules", *Chemical Society Reviews* 39:3810-3830 (2010).

Belcher R. et al., "A New Reagent for the Precipitation of Sulphate", *J. Chem. Soc.* pp. 4216-4218 (1952).

Benatti C.T. et al., "Sulfate Removal from Waste Chemicals by Precipitation", *Journal of Environmental Management* 90:504-511 (2009).

Berrocal M.J. et al., "Tripodal Ionophore with Sulfate Recognition Properties for Anion-Selective Electrodes", *Analytical Chemistry* 72(21):5295-5299 (Nov. 1, 2000).

Boari G. et al., "Advanced Evaporation Plants with Sulfate Removal by Ion Exchange", *Desalination* 19:283-298 (1976).

Boukhalfa C. et al., "Sulfate Removal from Aqueous Solutions by Hydrous Iron Oxide Macroscopic, Thermal and Spectroscopic Analyses", *Desalination* 214:38-48 (2007).

Byrne P. et al., "Gradual Transition from NH Pyridyl Hydrogen Bonding to the NH O Tape Synthon in Pyridyl Ureas", *Crystal Growth and Design* 8(9):3335-3344 (2008).

Custelcean R., "Anions in Crystal Engineering", *Chemical Society Reviews* 39:3675-3685 (2010).

(Continued)

*Primary Examiner* — David C Mellon
*Assistant Examiner* — Liam Royce
(74) *Attorney, Agent, or Firm* — Scully, Scott, Murphy & Presser, P.C.

(57) ABSTRACT

The present invention relates to urea-functionalized crystalline capsules self-assembled by sodium or potassium cation coordination and by hydrogen-bonding water bridges to selectively encapsulate tetrahedral divalent oxoanions from highly competitive aqueous alkaline solutions and methods using this system for selective anion separations from industrial solutions. The method involves competitive crystallizations using a tripodal tris(urea) functionalized ligand and, in particular, provides a viable approach to sulfate separation from nuclear wastes.

26 Claims, 6 Drawing Sheets

(56) References Cited

PUBLICATIONS

Custelcean R., "Current Opinion in Solid State and Materials Science", *Current Opinion in Solid State and Materials Science* 13:68-75 (2009).

Custelcean R. et al., "Selectivity Principles in Anion Separation by Crystallization of Hydrogen-Bonding Capsules", *J. Am. Chem. Soc.* 132:7177-7185 (2010).

Custelcean R. et al., "Anion Separation with Metal-Organic Frameworks", *Eur. J. Inorg. Chem.* pp. 1321-1340 (2007).

Custelcean R. et al., "Anion Coordination in Metal-Organic Frameworks Functionalized with Urea Hydrogen-Bonding Groups", *Crystal Growth & Design* 6(2):555-563 (2006).

Custelcean R. et al., "A Coordinatively Saturated Sulfate Encapsulated in a Metal-Organic Framework Functionalized with Urea Hydrogen-Bonding Groups", *Chem. Commun.* pp. 5971-5973 (2005).

Custelcean R. et al., "Selective Crystallization of Urea-Functionalized Capsules with Tunable Anion-Binding Cavities", *Crystal Growth & Design* 9(4):1985-1989 (2009).

Custelcean R. et al., "Sulfate Recognition by Persistent Crystalline Capsules with Rigidified Hydrogen-Bonding Cavities", *Angew. Chem. Int. Ed.* 47:1866-1870 (2008).

Darbi A. et al., "Sulfate Removal from Water", *Water Qual. Res. J. Canada* 38(1):169-182 (2003).

Delmau L.H. et al., "Robustness of the CSSX Process to Feed Variation: Efficient Cesium Removal from the High Potassium Wastes at Hanford", *Solvent Extraction and Ion Exchange* 28:19-48 (2010).

Haghsheno R. et al., "Study of Kinetic and Fixed Bed Operation of Removal of Sulfate Anions from an Industrial Wastewater by an Anion Exchange Resin", *Journal of Hazardous Materials* 166:961-966 (2009).

Hay B.P. et al., "Structural Design Criteria for Anion Hosts: Strategies for Achieving Anion Shape Recognition Through the Complementary Placement of Urea Donor Groups", *J. Am. Chem. Soc.* 127:1810-1819 (2005).

Hay B.P. et al., "Sulfate Removal Studies for River Protection Projection Part B1", *WSRC-TR-2000-00489*, Westinghouse Savannah River Company: Aiken, South Carolina (2001).

Jong T. et al., "Removal of Sulfate and Heavy Metals by Sulfate Reducing Bacteria in Short-Term Bench Scale Upflow Anaerobic Packed Bed Reactor Runs", *Water Research* 37:3379-3389 (2003).

Kang S.O. et al., "Cryptand-Like Anion Receptors", *Chemical Society Reviews* 39:3980-4003 (2010).

Lumetta G.J., "The Problem with Anions in the DOE Complex", *Fundamentals and Applications of Anion Separations* pp. 107-114 (2004).

Malaiyandi M., "Reverse Osmosis Separation of Sulfate, Nitrate, and Ammonia from Mining Effluents", *Separation Science and Technology* 16(4):371-376 (1981).

Manara D. et al., "Sulfur Behavior in Silicate Glasses and Melts: Implications for Sulfate Incorporation in Nuclear Waste Glasses as a Function of Alkali Cation and $V_2O_5$ Content", *Journal of Non-Crystalline Solids* 353:12-23 (2007).

Moyer B.A. et al., "Caustic-Side Solvent-Extraction Modeling for Hanford Interim Pretreatment System", *ORNL/TM-2008/073 Oak Ridge National Laboratory* (Jun. 2008).

Moyer B.A. et al., "Supramolecular Chemistry of Environmentally Relevant Anions", *Advances in Inorganic Chemistry* 59:175-204 (2006).

Pflugrath J.W. et al., "Sulphate Sequestered in the Sulphate-Binding Protein of *Salmonella typhimurium* is Bound Solely by Hydrogen Bonds", *Nature* 314:257-260 (Mar. 21, 1985).

Priyantha N. et al., "Removal of Sulfate, Phosphate and Colored Substances in Wastewater Effluents Using Feldspar", *Water Resources Management* 14:417-433 (2000).

Rajbanshi A. et al., "Structure and Selectivity Trends in Crystalline Urea-Functionalised Anion-Binding Capsules", *Supramolecular Chemistry* 24(1):65-71 (Jan. 2012).

Rajbanshi A. et al., "Sulfate Separation from Aqueous Alkaline Solutions by Selective Crystallization of Alkali Metal Coordination Capsules", *Crystal Growth & Design* 11:2702-2706 (2011).

Raposo C. et al., "Tris(2-Aminoethyl)Amine, a Suitable Spacer for Phosphate and Sulfate Receptors", *Chemistry Letters* pp. 759-760 (1995).

Ravikumar I. et al., "Recognition and Separation of Sulfate Anions", *Chem. Soc. Rev.* 41:3077-3098 (2012).

Tait S. et al., "Removal of Sulfate from High-Strength Wastewater by Crystallisation", *Water Research* 43:762-772 (2009).

Wang K.Y. et al., "Novel Polybenzimidazole (PBI) Nanofiltration Membranes for the Separation of Sulfate and Chromate from High Alkalinity Brine to Facilitate the Chlor-Alkali Process", *Ind. Eng. Chem. Res.* 46:1572-1577 (2007).

Walmarth W.R. et al., "Review: Waste-Pretreatment Technologies for Remediation of Legacy Defense Nuclear Wastes", *Solvent Extraction and Ion Exchange* 29:1-48 (2011).

Wu B. et al., "Sulfate Ion Encapsulation in Caged Supramolecular Structures Assembled by Second-Sphere Coordination", *Chem. Commun.* pp. 1762-1764 (2008).

\* cited by examiner

SELECTIVE OXOANION SEPARATION USING A TRIPODAL LIGAND

This invention was made with government support under Prime Contract No. DE-AC05-00OR22725 awarded by the U.S. Department of Energy. The government has certain rights in the invention.

FIELD OF THE INVENTION

The present invention relates to urea-functionalized crystalline capsules self-assembled by sodium or potassium cation coordination and by hydrogen-bonding water bridges to selectively encapsulate tetrahedral divalent oxoanions from highly competitive aqueous alkaline solutions and methods using this system for selective anion separations from industrial solutions. The method involves competitive crystallizations using a tripodal tris(urea) functionalized ligand and, in particular, provides a viable approach to sulfate separation from nuclear wastes.

BACKGROUND OF THE INVENTION

Supramolecular chemistry of anions is increasingly addressing utilitarian problems, generally related to health, environment, or energy. The challenge with real-world problems related to anion recognition is that they typically involve competitive aqueous environments. One problem of special interest is sulfate separation from radioactive wastes. Sulfate is a problematic component of legacy nuclear wastes, particularly those in the U.S. Department of Energy (DOE) complex, as it interferes with the vitrification process selected for waste disposal, increases the volume of waste forms that must be produced and stored, and reduces their geologic performance (Lumetta 2004; Moyer et al. 2006).

For example, the DOE has approximately 92 Mgal of alkaline high-level tank wastes left over from Cold War era weapons production. These wastes consist of sludges and soluble salts, the latter being approximately 85% of the volume of the waste and containing half the radioactivity. After removal of the preponderance of the radioactivity, mostly $^{137}$Cs, the salt waste can be stored in a low-activity waste form, borosilicate glass or saltstone. Owing to the high cost of producing glass, there is a need to maximize waste loading and to minimize the volume of glass.

Sulfate at high concentrations in nuclear waste is a significant determinant of the volume of glass that must be produced for certain waste feeds to vitrification (Lumetta 2004; Moyer et al. 2006). Above a loading of approximately 0.8% $SO_3$, separation of a sulfur-rich phase in the melter presents a significant electrode corrosion problem in vitrification, and corresponding insoluble, sulfur-rich phases in solidified glass degrade waste-form performance (Manara et al. 2007). Efficient removal of sulfate prior to vitrification therefore has the potential to benefit salt-waste processing by significantly reducing the mass of waste glass and processing costs (Hay et al. 2001).

In view of the potential cost savings to vitrification, economical methods for the removal of sulfate have been sought for more than a decade. This extremely challenging problem arises from the strongly hydrophilic nature of sulfate itself, as well as the high alkalinity, and the high concentration of competing anions such as nitrate, nitrite, carbonate, and aluminate found in the waste. Various techniques applicable at the industrial scale to sulfate removal from aqueous solutions include bioreduction, nanofiltration, reverse osmosis, adsorption, anion exchange, and crystallization (Darbi et al. 2003; Jong et al. 2003; Wang et al. 2007; Malaiyandi et al. 1981; Priyantha et al. 2000; Boukhalfa et al. 2007; Haghsheno et al. 2009; Boari et al. 1976; Tait et al. 2009; Benatti et al. 2009; Belcher et al. 1952). However, none have the requisite selectivity or are not operative under the conditions of high alkalinity and high ionic strength characteristic of nuclear waste.

Sulfate removal from aqueous solutions is already challenging enough due to the very strong hydration of this anion ($\Delta G°_h = -1080$ kJ/mol). The extreme ionic strength (>6 M) and alkalinity (pH 14) of the waste, as well as the high concentrations of competing anions (mainly $NO_3^-$, $NO_2^-$, $OH^-$, and $CO_3^{2-}$) further increase the complexity of the problem. Though examples of sulfate selective receptors have been previously reported (Ravikumar et al. 2012), none of them has been demonstrated to work in a viable binding-release cycle under the extremely demanding conditions found in nuclear wastes.

A promising approach to effective sulfate recognition and separation from competitive aqueous environments is to take inspiration from Nature's sulfate-binding protein (Pflugrath et al. 1985), and completely isolate the anion from the surrounding solvent by encapsulation inside structurally constrained cavities functionalized with complementary binding groups. Though such cryptand-like architectures (Kang et al., 2010) are often difficult to assemble via traditional organic synthesis, a more practical approach to cage receptors for anions via self-assembly from relatively simple building units has been recently demonstrated (Ballester 2010). Alternatively, self-assembly of crystalline solids that selectively include targeted anions upon crystallization can be effectively employed for anion separation (Custelcean 2010a; Custelcean 2009a; Custelcean et al. 2007). A distinct advantage of such crystalline 'hosts' is that the stiffer environment inside crystals may prevent the structural distortion of the anion-binding cavities and accommodation of competing anions, resulting in superior selectivity.

The tripodal ligand L1, consisting of a urea-functionalized tren scaffold (Raposo et al. 1995; Berrocal et al. 2000; Custelcean et al. 2005), has recently been reported to self-assemble with $Mg(H_2O)_6^{2+}$ cations and encapsulate sulfate upon crystallization from competitive aqueous solutions (Custelcean et al. 2008; Custelcean et al. 2010b). The rigid and highly complementary binding cavities of these crystalline capsules, comprising 12 urea hydrogen bonds to the sulfate, ensured exceptional sulfate selectivity based on shape, size, and charge discrimination. However, in spite of their excellent anion recognition abilities, these capsules have limited utility for sulfate separation from alkaline nuclear wastes, as they do not form under basic conditions (pH>10) due to $Mg(OH)_2$ precipitation.

However, it has now been found that alkali metal cations, which are tolerant to highly basic conditions, provide a viable solution to the problem of sulfate separation from nuclear waste. Since lithium and potassium are virtually absent in nuclear wastes (Custelcean et al. 2009b), a sodium-based system, in particular, takes advantage of the abundance of sodium ions in the waste, and not only circumvents the need for adding external ionic components to the waste, but significantly decreases the solubility of the capsules through the common ion effect.

The anion-binding cavities in the monovalent sodium- and potassium-based crystalline capsules provide good shape and size recognition for sulfate as had previously been seen in sulfate separation selectivity in competitive crystallizations using the divalent Mg-based system (Custelcean et al. 2008; Custelcean et al. 2010a; Rajbanshi et al. 2011). However, previous systems (Mg and Li) were not suitable for use under highly alkaline, aqueous conditions so these new sodium and potassium systems meet this unfilled need and also provide a system useful under neutral and alkaline conditions in the absence of divalent cations, and particularly in the absence of magnesium cations.

SUMMARY OF THE INVENTION

The present invention is directed to a method of selective anion separation from industrial solutions, and particularly from industrial waste, including nuclear waste and the Bayer liquor produced during bauxite processing for aluminum production. The invention also provides compositions having Na-based or K-based complexes represented by the formula $Na_2(anion)(L1)_2(H_2O)_4$ or $K_2(anion)(L1)_2(H_2O)_2$, respectively, where "anion" represents a tetrahedral divalent oxoanion, and L1 is the ligand (N-[2-[bis[2-[N'-(3-pyridyl)ureido]ethyl]-amino]ethyl]-N'-(3-pyridyl)urea). In certain embodiments, when the anion is a sulfate anion, the Na-based complex is $Na_2(SO_4)(L1)_2(H_2O)_4$ which is also referred to herein as Compound 1. For the K-based complex, the formula is $K_2(SO_4)(L1)_2(H_2O)_2$ which is also referred to herein as Compound 2.

Accordingly, the invention is directed to a method for selective anion separation which comprises (a) admixing L1 with an aqueous, highly alkaline solution for a time and in an amount sufficient to form a crystalline solid of $Na_2(oxoanion)(L1)_2(H_2O)_4$ or of $K_2(oxoanion)(L1)_2(H_2O)_2$, or of both; and (b) separating the crystalline solid from the solution. The aqueous, highly alkaline solution used in the method comprises at least a stoichiometric amount of $Na^+$ or $K^+$ ions, or both, a tetrahedral divalent oxoanion ("oxoanion") and competitive anions. Alternatively, the method can be conducted in the absence of divalent cations, e.g., $Mg^{2+}$, at neutral or alkaline pH. The oxoanions which can be selectively crystallized in accordance with the invention are divalent tetrahedral oxoanions, and include but are not limited to sulfate, selenate, chromate, tellurate, molybdate, and tungstate. In some embodiments the aqueous highly alkaline solution has a pH greater than 9.5; in other embodiments, the pH is about 14. In some embodiments, the concentration of $Na^+$ ions ranges from about 3-7 molar. In the embodiments for competitive solutions that lack Mg, neutral pH is about pH 7 and alkaline pH is any pH greater than 7.

Generally, the amount of L1 added is at least two equivalents per equivalent of oxoanion present in the solution. The proportion needs not be exactly 2:1 since the method is feasible with an excess of L1 or an excess of oxoanion. L1 can be added as a solid or as a concentrate in an organic solvent or in a mixed organic/aqueous solvent. When added as a solid, it can be granulated or powdered. In a preferred embodiment, L1 is added as a solid, and more preferably as a fine powder.

Examples of highly alkaline aqueous solutions in which oxoanions and other competitive ions are present include industrial waste solutions such as nuclear waste and Bayer liquor (from bauxite ore processing). Sulfate is selectively recovered from nuclear waste whereas both sulfate and chromate can be recovered from Bayer liquor.

Hence, the invention is also directed to a method of sulfate separation from nuclear waste by admixing L1 with a nuclear waste solution for a time and in an amount sufficient to form a crystalline solid of $Na_2(SO_4)(L1)_2(H_2O)_4$ and separating the crystalline solid from the nuclear waste solution. Advantageously, the L1 can be recovered and recycled back into the method of the invention, providing a cost and resource benefit. L1 can be recovered, for example, by recrystallization from water.

Another aspect of the invention is directed to a composition comprising a complex represented by the formula $Na_2(oxoanion)(L1)_2(H_2O)_4$ or $K_2(oxoanion)(L1)_2(H_2O)_2$, wherein the oxoanion is a tetrahedral divalent oxoanion, and L1 is (N-[2-[bis[2-[N'-(3-pyridyl)ureido]ethyl]-amino]ethyl]-N'-(3-pyridyl)urea). The tetrahedral, divalent oxoanion is selected from the group consisting of sulfate, selenate, chromate, tellurate, molybdate and tungstate. In a preferred embodiment, the complex is $Na_2SO_4(L1)_2(H_2O)_4$ or $K_2SO_4(L1)_2(H_2O)_2$.

DETAILED DESCRIPTION OF THE INVENTION

Figure 1:
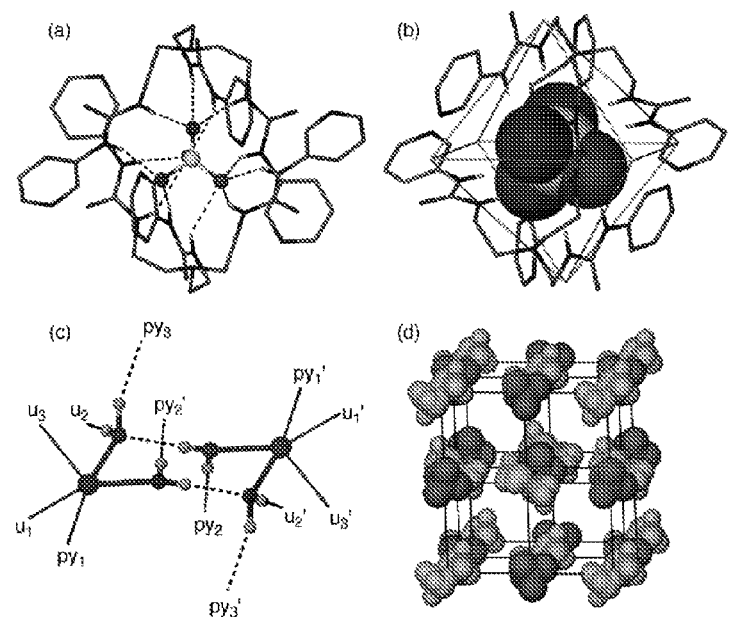
FIG. 1 provides the crystal structure of Compound 1. Panel (a) depicts sulfate encapsulation by 2 molecules of L1, with the formation of 12 hydrogen bonds from six urea groups. Panel (b) shows anionic $SO_4(L1)_2^{2-}$ secondary binding units (SBUs) showing the pseudooctahedral arrangement of the six pyridyl-C=O(urea) chelating groups externally functionalizing the capsule. The octahedron was drawn by connecting the six centroids defined by the N(py) and O(urea) atom pairs. Panel (c) shows cationic $Na_2(H_2O)_4^{2+}$ SBU and its interactions with the six pyridylurea chelating groups. Panel (d) illustrates the NaCl-type framework formed by octahedral connectivity of the anionic and cationic SBUs ($SO_4^{2-}$ and $Na_2(H_2O)_4^{2+}$ are shown in dark grey and light grey, respectively; L1 is omitted for clarity).

The inventors have established that the tripodal tris(urea) anion receptor L1 selectively crystallizes from competitive aqueous solutions with various $M_nSO_4$ salts (M=Mg, Ca, Zn, Co, Cd, Li, Na, K) into three-dimensional frameworks comprising anionic $SO_4(L1)_2^{2-}$ capsules linked by $M(H_2O)_6^{2+}$ (M=Mg, Ca, Zn, Co, Cd), $Li(H_2O)^+$, $Na_2(H_2O)_4^{2+}$, or $K_2(H_2O)_2^{2+}$ hydrated cations. The work with the Na and K complexes lead to development of the present invention for recovering oxoanions from highly alkaline, competitive aqueous solutions such as those found in certain industrial wastes, and importantly, provides an economical and a much-needed technology for sulfate separation from nuclear wastes. Besides meeting these demanding conditions, the Na- and K-based systems offer the additional advantage of the organizational rigidity of the crystalline state, which restricts the structural flexibility of the binding sites and accommodation of competing anions, thereby resulting in superior anion selectivity.

Accordingly, one aspect of the invention is directed to a method of selective anion separation from aqueous industrial solutions that are highly alkaline. This method comprises (a) admixing L1 with an aqueous, highly alkaline solution, which solution comprises at least a stoichiometric amount of $Na^+$ or $K^+$ ions, or both, a tetrahedral divalent oxoanion ("oxoanion") and competitive anions, for a time and in an amount sufficient to form a crystalline solid comprising $Na_2$(oxoanion)$(L1)_2(H_2O)_4$ or of $K_2$(oxoanion)$(L1)_2(H_2O)_2$, or of both; and (b) separating the crystalline solid from the remaining solution, wherein L1 is (N-[2-[bis[2-[N'-(3-pyridyl)ureido]ethyl]-amino]ethyl]-N'-(3-pyridyl)urea).

Additionally, the invention provides a method of selective anion separation from neutral or alkaline, aqueous industrial solutions that lack magnesium or other divalent metal cations ($M^{2+}$). This method comprises (a) admixing L1 with an aqueous neutral or alkaline solution lacking divalent cations, or any substantial amount of divalent cations, which solution comprises at least a stoichiometric amount of $Na^+$ or $K^+$ ions, or both, a tetrahedral divalent oxoanion ("oxoanion") and competitive anions, for a time and in an amount sufficient to form a crystalline solid comprising $Na_2$(oxoanion)$(L1)_2(H_2O)_4$ or of $K_2$(oxoanion)$(L1)_2(H_2O)_2$, or of both; and (b) separating the crystalline solid from the remaining solution, wherein L1 is (N-[2-[bis[2-[N'-(3-pyridyl)ureido]ethyl]-amino]ethyl]-N'-(3-pyridyl)urea).

As used herein, anion selectivity arises from the preference for L1 to bind tetrahedral divalent oxoanions over other, non-tetrahedral or non-divalent anions that are present in a solution and to form crystals upon such binding. This selectivity need not produce 100% removal of the oxoanions nor does selectivity mean that other anions can not be present in the resultant crystalline solid obtained with the method of the invention (e.g., bind L1 or contaminate the crystalline). Rather, anion selectivity, as used herein, is sufficient to functionally provide preferential removal of a substantial portion of oxoanions from a competitive solution such that at least about 30, 40, 50, 60, 70, 80, 90, 95, 98, or 99 per cent or more of the oxoanions can be separated from the solutions as a solid with L1. The amount of the oxoanion that can be removed can be further increased by repeatedly adding fresh or recovered L1 to the solution and recovering the solid L1-oxoanion complex. The ability to recover and recycle L1 is an advantage that decreases the effective cost of oxoanion removal (or recovery of the oxoanion if that is the intended goal).

Further, anion selectivity also refers to the ability of L1 to preferentially bind one tetrahedral, divalent oxoanion over a second, different tetrahedral, divalent oxoanion in the solution. For example, in a Na-based competitive crystallization, L1 preferentially binds sulfate over selenate at a ratio of about 31:1; in the K-based system the ratio is 13:1. For comparison in the Mg-based system, which is not functional under the highly alkaline pH conditions used in certain embodiments of the present invention, the ratio drops to 3:1. Accordingly, the method of the invention can also be used to selectively separate, i.e., differentially remove, substantial amounts of one tetrahedral, divalent anion in the presence of other oxoanions in the same aqueous environment.

The tetrahedral, divalent oxoanions that can be selectively separated from a competitive ionic solution using L1 are selected from the group consisting of sulfate, selenate, chromate, tellurate, molybdate and tungstate. The chemical formulas of these ions are $SO_4$, $SeO_4$, $CrO_4$, $TeO_4$, $MoO_4$, and $WO_4$, respectively. Each of these anions are divalent, meaning a charge of −2.

As used herein, highly alkaline means having a pH greater than about 9.5. The pH of such highly alkaline solutions range from 9.5 to 14, and can be about 10, 10.5, 11, 11.5, 12, 12.5, 13, 13.5 or 14. In certain embodiments the pH is about 14. The typical pH of industrial waste solutions are known in the art, can be easily determined and can be adjusted to highly alkaline, if necessary. As used herein, neutral pH is 7 or within 0.1-0.2 pH units of 7. As used herein, alkaline means greater than pH 7. Hence an alkaline solution can have a pH ranging from greater than 7 to as high as pH 14. The methods for determining pH and adjusting pH are well known in the art.

L1 is a tripodal tris(urea) anion receptor. The chemical name for L1 is N-[2-[bis[2-[N'-(3-pyridyl)ureido]ethyl]-amino]ethyl]-N'-(3-pyridyl)urea) and its structure is shown below:

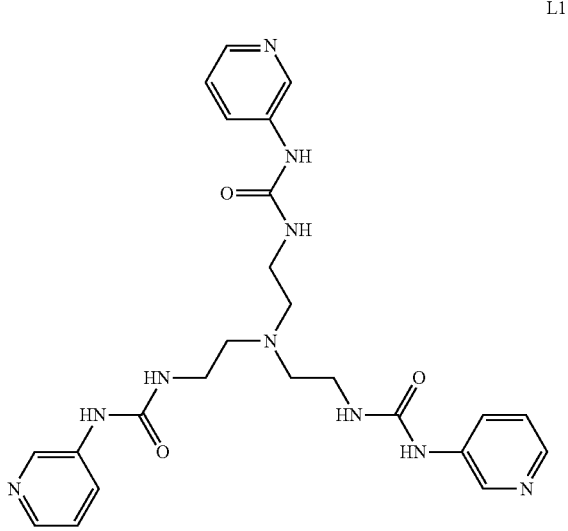 [SMILES: O=C(NCCN(CCNC(=O)Nc1cccnc1)CCNC(=O)Nc1cccnc1)Nc1cccnc1]

L1

L1 is anion selective for tetrahedral, divalent oxoanions present in competitive solutions, and moreover, can be used to preferentially separate those oxoanions out of the solution under highly alkaline conditions when complexed with sodium or potassium ions. Investigations of other ligands similar to L1 did not exhibit such selectivity under these conditions. Likewise, use of L1 with other metal ions was found ineffective at these high pHs, typically due to the formation of other by products (e.g., Mg forms insoluble $Mg(OH)_2$ under highly alkaline conditions).

A competitive solution is a solution which contains ions that compete for binding to or interact with the same ligand or binding partner. For example, the major competing anions in nuclear waste are sulfate, nitrate, nitrite, carbonate, and aluminate found in the waste.

An example of a competitive solution that presents a challenge for oxoanion recovery is an aqueous solution which, in addition to the oxoanions, contains ~6 M $Na^+$, multiple anions (nitrate, nitrite, carbonate, aluminates) and has a pH of 14.

Industrial solutions that contain competitive ions include, but are not limited to, nuclear waste, Bayer liquor produced during bauxite processing, sulfate-rich industrial waste waters, such as may be found in mining or ore waste waters, flue gas scrubber solutions and other waste waters containing tetrahedral divalent oxoanions (sulfate, selenate or other oxoanions). Nuclear waste and Bayer liquor are highly alkaline. For industrial solutions which are neutral or alkaline and lack divalent metal cations or any substantial quantity of such divalent cations, L1 can be added in accordance with the methods of the invention to achieve selective anion separation. Solutions which contain magnesium or $M^{2+}$ can be made highly alkaline by adding a base (e.g., by adding NaOH pellets, KOH pellets or a concentrated solution of these bases) in sufficient quantity to bring the solution to an appropriate pH for practicing the method of the invention for highly alkaline solutions since the presence of divalent metal cations does not interfere with the formation of the crystalline solids at high pH. Industrial wastes are often subject to multiple processing steps to remove or recover particular components from the waste. Hence, the present methods can be used in conjunction with these other processing steps, as appropriate, and at any convenient stage in the processing as will be readily apparent to those of skill in the art.

Nuclear wastes include those stored at the Hanford Site, at the Savannah River site or at other sites in the world. The components of nuclear waste, particularly the waste solutions stored at Hanford and Savannah River, are well-documented to be competitive, highly alkaline, aqueous solutions.

To practice the present invention, the amount of L1 needed is determined by the expected amount of oxoanions present in the solution to be treated. L1 crystallizes with the oxoanions in a 2:1 stoichiometry so at least two equivalents of L1 should be added per expected equivalent of oxoanion, although the method works with a molar excess of either L1 or the oxoanion. The Na and K ions may be present in stoichiometric amounts (1:1 with L1) or in significant molar excess depending on the nature of the solution being treated. Hence, the amounts of Na or K can range from a few millimolar, if the amount of oxoanion is in that same millimolar range, or the amount of Na and K can be in the molar range when millimolar amounts of oxoanion are present. The method advantageously and preferably uses solid L1 since that does not increase the solution volume and is convenient, especially for nuclear waste in which minimal manipulations are desirable. Solid L1 can be in pieces, granulated, powdered and the like. Further, the method can also be practiced by dissolving L1 in an organic solvent (such as MeOH, or DMSO), or mixed organic aqueous solvents, such as $MeOH/H_2O$ and adding the solvent directly to the solution to be treated:

If applicable, L1 is added at the same time as or just after adjusting the solution to be highly alkaline.

L1 is admixed with the aqueous solution used in the invention by stirring, mixing, blending, vortexing, magnetic stirring or the like technique that allows L1 to be distributed throughout the solution. The method of mixing can be determined by those of skill in the art, based on the volumes of solution being handled, the conditions under which the solution is stored and the available mixing apparatus. Stirring solutions and mixing components on an industrial scale are known in the art. On a small scale, magnetic stirrers, overhead stirrers, shakers, vortexes and the like are well known. The mixing is continued for a time sufficient to allow the L1 to form a crystalline complex with the Na or K ions and the tetrahedral, divalent oxoanions present in the competitive solution. While this time period for formation of the crystalline solid complex can vary, depending on the solution, oxoanion to be recovered and relative amounts of the various components in the solution, formation can be readily followed by techniques known in the art. For example, powder X-ray diffraction (PXRD) can be used to follow formation of the complex (as well as dissolution of the solid L1 if used in the method). The time for reaching completion or equilibrium can range from a few hours to a few weeks and is thus ascertained by the monitoring technique. For example, Compound 1 can be observed by PXRD in waste simulants within about 2 days and appears to reach complete formation with disappearance of solid L1 in about 4 days (see Examples and FIG. 3).

Once the reaction has gone to completion or reached equilibrium, the crystalline solid is separated or recovered from the solution. Such methods are known in the art and include filtration, countercurrent decantation, centrifugation and solid settlement and removal from the solution. By recovering the crystalline solid formed in the methods of the invention, and separating it from the solution, selective anion separation is achieved since the competitive anions remain in solution and the oxoanions are recovered in the crystalline solid complex. While the crystalline solid can be discarded, it is actually advantageous to use it for recovering and recycling L1. To recycle L1, the crystalline solid, for example, is washed and L1 recrystallized from fresh water leaving an aqueous solution of $Na_2$(oxoanions), $K_2$(oxoanion) or both. Any method of recovering L1 can be used. Hence, L1 can be recrystallized from other solvents or isolated chromatographically, as may be convenient, or known to those of skill in the art.

Accordingly, some embodiments of the invention include repeating the methods of the invention using fresh L1 or recovered L1. In other words, the competitive aqueous solutions can be subjected to multiple crystallization and recovery cycles in accordance with the methods of the invention.

Since alkali metal cations are tolerant to highly basic conditions, crystallization with these cations is particularly advantageous for sulfate separation from nuclear wastes, as it benefits from the abundance of sodium cations in the waste. Thus, there are some clear advantages for employing a Na-based crystallization system to form Compound 1 in particular and for the method of the invention in general. First, no external ionic components need to be added to the waste (or solution), thereby minimizing volume. Moreover, the increment of sodium removal from the waste (or solution) is itself mildly beneficial in reducing the waste's volume. Second, the high sodium concentration in the waste is expected to decrease the solubility of Compound 1 through the common ion effect, which would increase the sulfate separation efficacy.

Further embodiments of the invention provide a method of sulfate separation from nuclear waste which comprises (a) admixing L1 with a nuclear waste solution for a time and in an amount sufficient to form a crystalline solid of $Na_2(SO_4)$ $(L1)_2(H_2O)_4$; and (b) separating the crystalline solid from the nuclear waste solution. These methods are conducted as described above, and can include a further step of recovering and recycling L1 from the crystalline solid as described above.

Another aspect of the invention relates to the composition comprising a complex represented by the formula $Na_2$(anion)$(L1)_2(H_2O)_4$ or $K_2$(anion)$(L1)_2(H_2O)_2$, wherein anion is a tetrahedral divalent oxoanion, and L1 is (N-[2-[bis[2-[N'-(3-pyridyl)ureido]ethyl]-amino]ethyl]-N'-(3-pyridyl)urea).

The compositions of the invention can be prepared by a variety of methods. For example, the complex can be recovered in accordance with the methods of the invention or can be prepared by crystallization from another solvent or solvent system. For example, slow evaporation of water/methanol (1:1) solutions containing stoichiometric amounts of L1 and $Na_2SO_4$ or $K_2SO_4$ affords crystals with the composition $Na_2SO_4(L1)_2(H_2O)_4$ (Compound 1), or $K_2SO_4(L1)_2(H_2O)_2$ (Compound 2), respectively, as determined by single-crystal X-ray diffraction and elemental analysis. The solvent composition appears to be important for the formation of these complexes since solutions containing crystallized Compound 1 or Compound 2 that are left open to allow the methanol solvent to almost completely evaporate, results in dissolution of those crystals and formation of crystals of $L1.(H_2O)_2$, which have a lower water solubility. Other solvent systems for recovering Compounds 1 and/or 2 can be used and determined by those of skill in the art.

The present invention thus demonstrates that crystallization of $SO_4(L1)_2^{2-}$ capsules offers an effective approach to sulfate separation from alkaline solutions as found in the Hanford waste as well as separation of other oxoanions from highly alkaline aqueous solutions. The crystallization process can be tailored for various waste compositions by choosing the appropriate metal cation component. While crystallization using a magnesium-based system works exceptionally well in mildly basic solutions, such a system is not useful under highly alkaline conditions. Even so, the Mg-based system was used to demonstrate that L1 can be easily recovered in high yields and recycled without any notable loss of activity for at least three cycles. Sulfate separation from highly alkaline and complex solutions that more closely simulate the Hanford waste compositions are achieved by crystallization of the sodium-based crystalline Compound 1. While the more hydrophilic aluminate and carbonate anions, which are both present in significant amounts in the Hanford waste, were found to interfere with the crystallization of Compound 1, by preferentially salting out $L1.2H_2O$, the less hydrophilic nitrate, the most abundant anion in the waste, was found to have a beneficial effect, preferentially salting out crystalline Compound 1.

Overall, crystallization of Compound 1 is sufficient to provide a much-needed technology for selective sulfate separation from Hanford tank wastes and to provide a reliable and economical separation process with negligible loss of ligand and good removal of sulfate.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications of other documents cited are herein incorporated by reference in their entirety.

EXAMPLES

General Methods

All reagents and solvents were purchased from commercial sources and used without further purification. $^1H$ NMR spectra were collected on a Bruker 400 MHz spectrometer. Melting points were measured on a Uni-Melt Thomas Hoover capillary melting point apparatus and are uncorrected. Powder X-ray diffraction (PXRD) patterns were collected at room temperature on a Bruker D5005 diffractometer using monochromatic Cu Kα (λ=1.5418 Å). FT-IR spectra were recorded in KBr pellets using a Digilab FTS 7000 spectrometer. Elemental analyses were performed by Galbraith Laboratories, Inc.

L1 was synthesized using a modified published procedure (Custelcean et al. 2009b; Wu et al. 2008). Briefly, nicotinyl azide (Custelcean et al. 2006; Byrne et al. 2008) (13.1 g, 0.0884 mol) was dissolved in anhydrous toluene (150 mL) and refluxed at 110° C. for two hours, until no more nitrogen evolved. The solution was subsequently cooled to 60° C. and tris(2-aminoethyl)amine (3.7 mL, 0.0247 mol) was added at once to immediately yield a light yellow precipitate. The reaction mixture was stirred at the same temperature for 1 h, and then cooled to room temperature. The precipitate was filtered and recrystallized from $MeOH/H_2O$ (1:4) to yield 10.2 g (76%) of $L1.2H_2O$ as a white crystalline solid. Single-crystal X-ray diffraction (described below) and PXRD confirmed that the product was the dihydrate of L1. $^1$1-1 NMR (δH; 400 MHz, d6-DMSO, 25° C.): 8.73 (s, 3H; NH), 8.51 (d, J=2.53 Hz, 3H; CH), 8.09 (d, J=4.66 Hz, 3H; CH), 7.86 (d, J=7.69 Hz, 3H; CH), 7.21 (dd, J=4.69, 7.04 Hz, 3H; CH), 6.29 (t, J=5.36 Hz, 3H; NH), 3.20 (dt, J=6.13, 6.03 Hz, 6H; $CH_2$), 2.59 (t, J=6.54 Hz, 6H; $CH_2$).

Example 1

Synthesis of $Na_2SO_4(L1)_2(H_2O)_4$ (Compound 1)

$L1.2H_2O$ (30.0 mg, 0.055 mmol) and $Na_2SO_4$ (4.0 mg, 0.028 mmol) were dissolved in 3 mL of $H_2O/MeOH$ (1:1, v/v). The resulting solution was warmed and allowed to slowly evaporate at room temperature. Upon evaporation of about ⅓ of the total solvent volume, colorless crystals of Compound 1 formed, which were filtered, washed with water, and dried. Yield: 20 mg (59%). Mp: 170-172° C. FT-IR (KBr): ν=1095 $cm^{-1}$ ($SO_4^{2-}$). Elemental analysis (%) calcd for $Na_2SO_4(L1)_2(H_2O)_4$: C 46.98, H 5.58, N 22.83, S 2.61, Na 3.75; found: C 46.51, H 5.53, N 22.48, S 2.62, Na 3.76.

Example 2

Synthesis of $K_2SO_4(L1)_2(H_2O)_2$ (Compound 2)

$L1.2H_2O$ (25.0 mg, 0.046 mmol) and $K_2SO_4$ (4.0 mg, 0.023 mmol) were dissolved in 3 mL of $H_2O/MeOH$ (1:1, v/v). The resulting solution was warmed and allowed to slowly evaporate at room temperature. Upon evaporation of about ⅓ of the total solvent volume, colorless crystals of Compound 2 formed, which were filtered, washed with water, and dried. Yield: 12 mg (43%). Mp: 186-188° C. FT-IR (KBr): ν=1098 $cm^{-1}$ ($SO_4^{2-}$). Elemental analysis (%) calcd for $K_2SO_4(L1)_2(H_2O)_2$: C 47.12, H 5.27, N 22.90, S 2.62, K 6.39; found: C 46.84, H 5.20, N 22.42, S 2.49, K 6.08.

Example 3

Single-Crystal X-Ray Structural Determination

Single crystals of $L1.2H_2O$, were grown by slow evaporation of a $H_2O/MeOH$ (1:1, v/v) solution.

Single crystals of Compound 1 and Compound 2 were grown by slow evaporation of $H_2O/MeOH$ (1:1, v/v) solutions containing stoichiometric amounts of $Na_2SO_4$ or $K_2SO_4$, respectively.

Single-crystal X-ray data were collected on a Bruker SMART APEX CCD diffractometer with fine-focus Mo Kα radiation ($\lambda$=0.71073 Å), operated at 50 kV and 30 mA. The structures were solved by direct methods and refined on $F^2$ using the SHELXTL software package (SHELXTL 6.12; Bruker AXS, Inc., Madison, Wis.). Absorption corrections were applied using SADABS, part of the SHELXTL package. All non-hydrogen atoms were refined anisotropically. Hydrogen atoms were placed in idealized positions and refined with a riding model, except for the water protons, which were located from the difference Fourier maps and refined isotropically.

Crystal data for $L1.2H_2O$: $C_{24}H_3N_{10}O_5$, M=542.61, colorless prism, 0.18×0.15×0.14 mm$^3$, triclinic, space group P-1 (No. 2), a=8.4436(5), b=12.2377(8), c=13.6622(8) Å, α=95.3550(10), β=100.0760(10), γ=105.0520(10)°, V=1327.88(14) Å$^3$, Z=2, $D_c$=1.357 g/cm$^3$, $F_{000}$=576, T=173 (2) K, $2\theta_{max}$=56.7°, 9055 reflections collected, 6511 unique ($R_{int}$=0.0217). Final GOF=1.037, $R_1$=0.0625, $wR_2$=0.1286, R indices based on 4883 reflections with I>2σ(I) (refinement on $F^2$), 368 parameters, 0 restraints. Lp and absorption corrections applied, μ=0.099 mm$^{-1}$.

Crystal data for Compound 1: $C_{24}H_{34}N_{10}NaO_7S_{0.50}$, M=613.63, colorless prism, 0.21×0.18×0.16 mm$^3$, monoclinic, space group P2$_1$/n (No. 14), a=12.1207(6), b=18.8019 (9), c=13.2832(7) Å, β=91.6320(10)°, V=3025.9(3) Å$^3$, Z=4, $D_c$=1.347 g/cm$^3$, $F_{000}$=1292, T=173(2) K, $2\theta_{max}$=56.6°, 24250 reflections collected, 7505 unique ($R_{int}$=0.0347). Final GOF=1.012, $R_1$=0.0513, $wR_2$=0.1153, R indices based on 5860 reflections with I>2 sigma(I) (refinement on $F^2$), 410 parameters, 0 restraints. Lp and absorption corrections applied, μ=0.146 mm$^{-1}$.

Crystal data for Compound 2: $C_{24}H_{32}KN_{10}O_6S_{0.50}$, M=611.73, colorless prism, 0.23×0.12×0.06 mm$^3$, monoclinic, space group P2$_1$/n (No. 14), a=11.9118(7), b=18.5604 (11), c=12.8360(7) Å, β=91.6400(10)°, V=2836.7(3) Å$^3$, Z=4, $D_c$=1.432 g/cm$^3$, $F_{000}$=1284, T=173(2) K, $2\theta_{max}$=56.7°, 16432 reflections collected, 7020 unique ($R_{int}$=0.0361). Final GOF=1.019, $R_1$=0.0471, $wR_2$=0.1086, R indices based on 5186 reflections with I>2σ(I) (refinement on $F^2$), 402 parameters, 0 restraints. Lp and absorption corrections applied, μ=0.282 mm$^{-1}$.

The crystal structure of Compound 1 (FIG. 1) comprises anionic $SO_4(L1)_2^{2-}$ and cationic $Na_2(H_2O)_4^{2+}$ secondary building units (SBUs) interconnected by coordination and hydrogen bonds into a three-dimensional framework with NaCl-type topology. The anionic SBU consists of an $SO_4^{2-}$ anion encapsulated by two embracing L1 molecules (FIG. 1a). This results in 12 complementary hydrogen bonds between the six chelating urea groups and $SO_4^{2-}$, which represents the preferred coordination number of sulfate according to electronic-structure calculations (Hay et al. 2005). However, as in other sulfate-encapsulating structures of L1 (Mg, Li), the orientation of the urea groups deviates from the ideal tetrahedral arrangement requiring each of the six ureas to chelate an O—S—O edge of the sulfate. Instead, the two L1 ligands are symmetry-related by an inversion center, resulting in distorted hydrogen-bonding geometries for three of the urea groups (lower half in FIG. 1a), with two of them chelating O vertices rather than O—S—O edges from sulfate. Another consequence of this centrosymmetric arrangement is that sulfate, which lacks an inversion center, is rotationally disordered over two positions to emulate the symmetry of the capsule. Though not ideal, this anion-binding geometry provides good shape and size recognition for sulfate.

The $SO_4(L1)_2^{2-}$ SBU is externally functionalized with six electron-donating pyridyl and C═O (urea) pairs, defining six chelating groups arranged in a pseudooctahedral geometry around the sulfate capsule (FIG. 1b). These groups can engage in metal coordination or hydrogen bonding, thereby forming three-dimensional frameworks in which the $SO_4(L1)_2^{2-}$ capsules act as 6-connecting nodes. As depicted in FIG. 1c, the SBUs of Compound 1 are cyclic chair-shaped hexanuclear clusters consisting of two Na$^+$ cations linked by two hydrogen-bonded water dimers. The clusters act as pseudooctahedral 6-connecting nodes linking six pyridyl-urea chelating groups from different anionic capsules via Na coordination (py$_1$-u$_1$, py$_1$'-u$_1$'), water hydrogen bonding (py$_2$-u$_2$, py$_2$'-u$_2$'), or a combination of the two interactions (py$_3$-u$_3$, py$_3$'-u$_3$').

Figure 2:
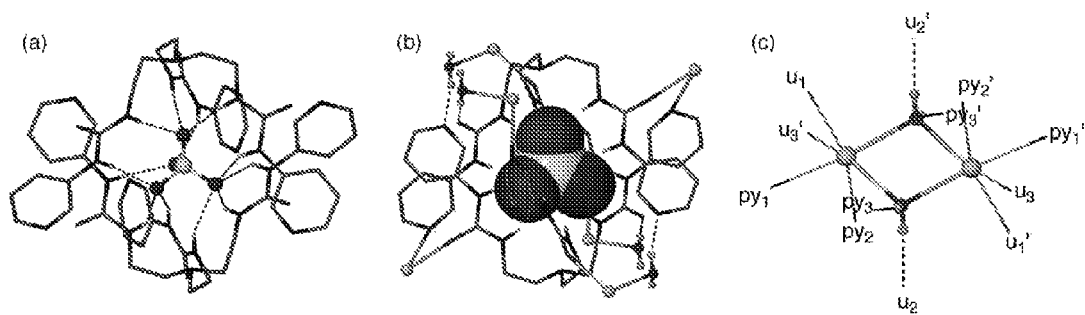
FIG. 2 provides the crystal structure of Compound 2. Panel (a) depicts sulfate encapsulation by 2 molecules of L1, with the formation of 12 hydrogen bonds from six urea groups. Panel (b) shows the pseudooctahedral capsule held together by K coordination and water hydrogen bonding. Panel (c) illustrates the $K_2(H_2O)_2^{2+}$ cluster and its interactions with the six pyridylurea chelating groups.

The crystal structure of Compound 2 consists of similar anionic $SO_4(L1)_2^{2-}$ cages interconnected into a NaCl-type framework by $K_2(H_2O)_2^{2+}$ cationic clusters (FIG. 2). The sulfate anions are encapsulated via 12 hydrogen bonds from the six urea groups lining the internal cavities of the capsules (FIG. 2a). Once again, due to the inversion symmetry of the capsules, three of the urea groups (lower half in FIG. 2a) deviate from the tetrahedral arrangement required for optimal sulfate binding, either displaying distorted hydrogen bonding parameters, or switching from an edge binding to a vertex binding mode. The outer surface of the capsules is decorated with six chelating pyridyl-C═O (urea) groups oriented in a pseudooctahedral symmetry. This geometry is evidently quite persistent, having been identified in a number of different sulfate-binding capsules made from L1 in the presence of various external cations. In the present case, the cations consist of $K_2(H_2O)_2^{2+}$ clusters acting as pseudooctahedral 6-connecting nodes. The cationic clusters link the sulfate capsules via K coordination by pyridyl and urea (py$_1$-u$_1$, py$_1$'-u$_1$'), K coordination by pyridyl and water hydrogen bonding to urea (py$_2$-u$_2$, py$_2$'-u$_2$'), or K coordination by urea and water hydrogen bonding to pyridyl (py$_3$-u$_3$, py$_3$'-u$_3$').

Example 4

Sulfate Separation Under Nuclear Waste Simulant Conditions Using Compound 1

To investigate crystallization of Compound 1 with L1 for sulfate separation under conditions similar to those found in nuclear waste, solid $L1.2H_2O$ (239 mg, 0.44 mmol) was added to 5 mL aqueous solution containing 5 M NaNO$_3$, 1.25 M NaOH, and 0.044 M Na$_2$SO$_4$. The measured pH of the solution was 14. This aqueous solution simulates the tank waste in terms of the $SO_4^{2-}$, OH$^-$, and Na$^+$ concentrations, as well as the high alkalinity (pH 14) (Bunker et al. 1995; Wilmarth et al. 2011; Delmau et al. 2010). The very high nitrate to sulfate molar ratio of 114 found in this simulant is also in line with the highly competitive conditions found in the actual waste.

The solid L1 and solution were magnetically stirred at room temperature and the reaction progress was monitored by PXRD. Complete conversion of L1.2H$_2$O into Compound 1 was achieved after 4 days of stirring. The crystalline product was filtered, washed with water, and dried, to yield 241 mg (90% based on L1.2H$_2$O) of Compound 1. Mp: 167-169° C. FT-IR (KBr): ν=1097 cm$^{-1}$ (SO$_4^{2-}$).

Figure 3:
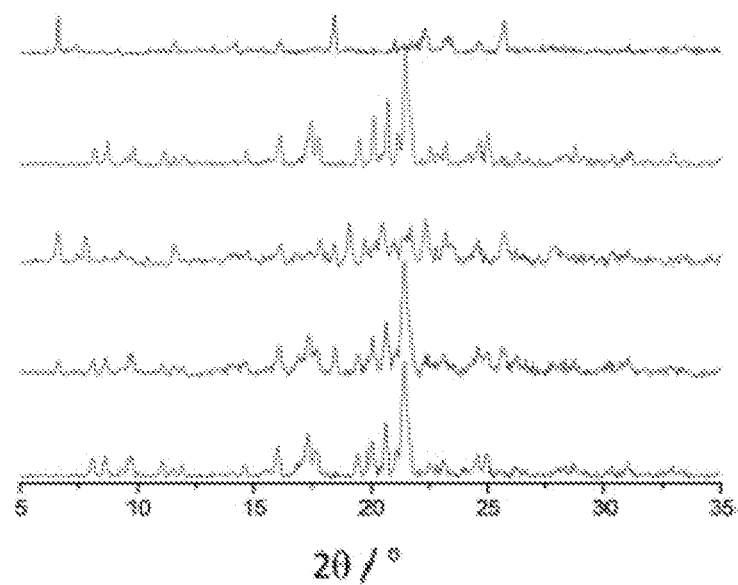
FIG. 3 shows the powder X-ray diffraction (PXRD) patterns for the conversion of L1.$2H_2O$ into Compound 1 during sulfate separation from a nuclear waste simulant. The traces, from top to bottom are: initial L1.$2H_2O$; reference Compound 1; crystalline mixture after 2 days of stirring; crystalline mixture after 3 days of stirring; final crystalline solid after 4 days of stirring. The bottom pattern shows no trace of L1.$2H_2O$, and is a virtually identical to the pattern of Compound 1 (second line from top).
Figure 4:
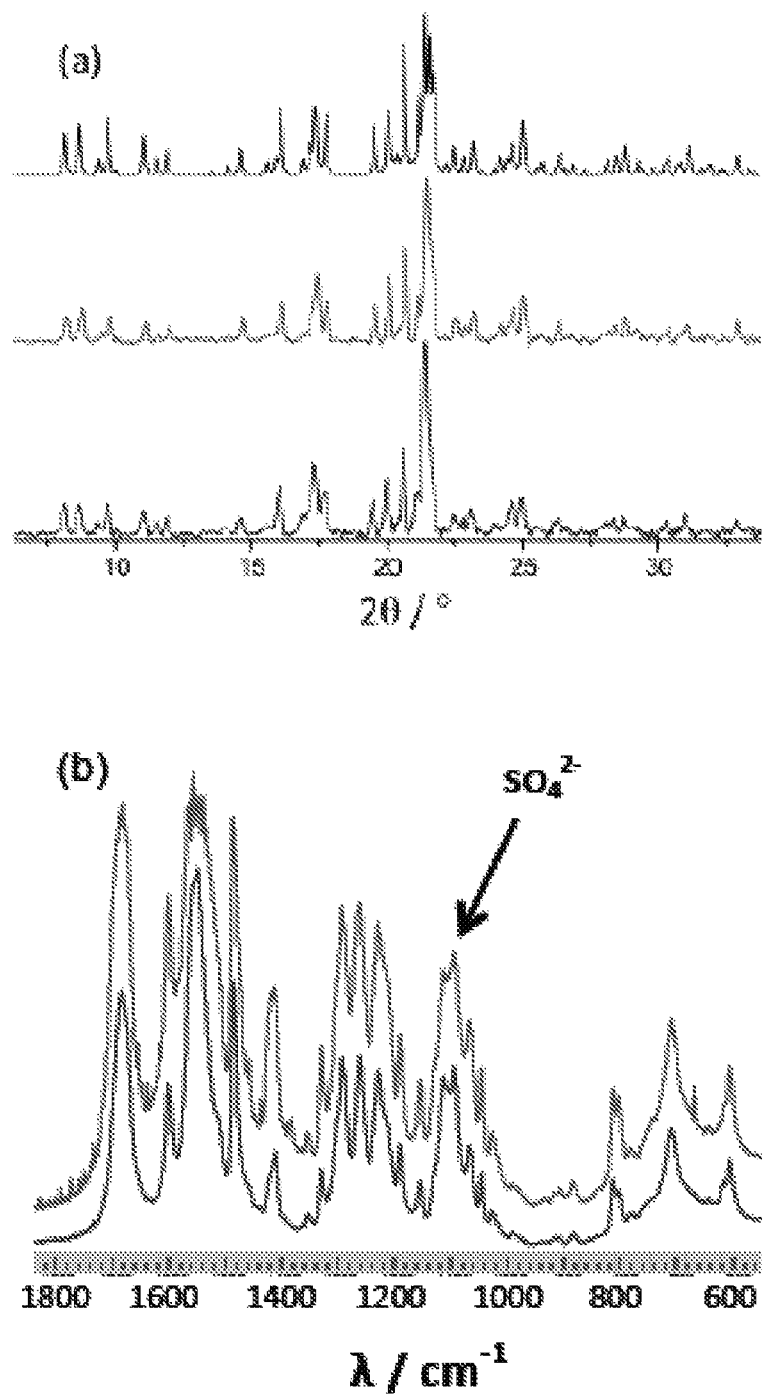
FIG. 4(a) provides a simulated PXRD from a single-crystal X-ray of Compound 1 (top), the experimental pattern from Compound 1 (middle), and the experimental pattern from the crystalline solid isolated from a nuclear waste simulant (bottom).
FIG. 4(b) shows the FT-IR spectra of Compound 1 (bottom) and the crystalline solid isolated from a nuclear waste simulant (top).

The PXRD pattern of Compound 1 started to emerge in 1-2 days, while the intensities of the peaks corresponding to L1 slowly decreased, completely disappearing after 4 days (FIG. 3). The final crystalline solid was isolated in 90% yield, and its PXRD and FTIR spectra corresponded to those of pure Compound 1 (FIG. 4). The relatively long reaction time required to convert L1 to Compound 1 appeared to proceed via a three-phase process involving slow dissolution of L1 and its recrystallization into Compound 1. While L1 is less soluble than Compound 1 in pure water, the large excess of sodium cations in the waste simulant apparently reversed this order, favoring the crystallization of Compound 1, presumably through the common ion effect.

Example 5

L1 Ligand Recycling

Figure 5:
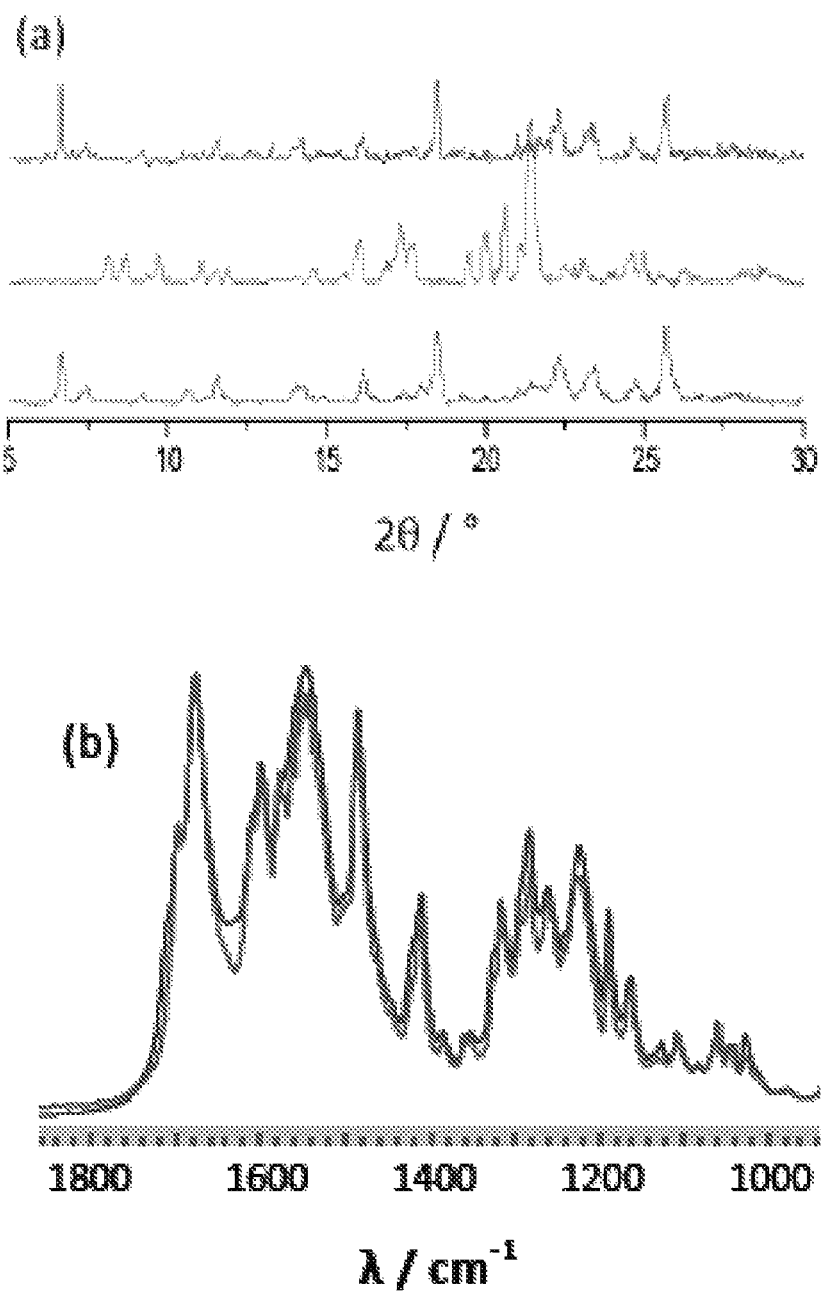
FIG. 5 illustrates the recovery of L1. Panel (a) shows the PXRD patterns reference L1.$2H_2O$ (top); resulting Compound 1 (middle); and L1.$2H_2O$ recovered from Compound 1 by stirring with water for 24 hrs (bottom). Panel (b) provides an overlay of FT-IR spectra for reference L1.$2H_2O$ and recovered L1.$2H_2O$.

To recover L1, a suspension of finely ground Compound 1 (200 mg, 0.163 mmol) in 6 mL of water was stirred for 24 h at room temperature. The resulting solid was filtered, washed with water, dried, and analyzed by PXRD and FTIR spectroscopy (FIG. 5). Yield: 162 mg (92%). The ligand was recovered in almost quantitative yield as crystalline L1, leaving aqueous Na$_2$SO$_4$.

Example 6

L1 Recycling from a Mg-Based System

For comparison purposes, solid L1.2H$_2$O (478 mg, 0.88 mmol) and Mg(NO$_3$)$_2$ (113 mg, 0.44 mmol) were added to 10 mL of Simulant 1 solution (Table 1) containing 0.44 mmol SO$_4^{2-}$. The mixture was stirred magnetically at room temperature for 48 h, and the resulting solid was filtered, washed with water, and dried. The identity of the crystalline product, MgSO$_4$(L1)$_2$(H$_2$O)$_6$ (Compound 3) was confirmed by PXRD and FTIR spectroscopy.

To recover and recycle L1, crystals of Compound 3 (457 mg, 0.368 mmol) were dissolved in 1 M HNO$_3$ (1 mL) to form a clear solution to which was added 1 M NaOH (2 mL). The mixture was stirred at room temperature overnight, and the resulting solid was filtered, washed with water, and dried. Yield: 388 mg. PXRD and NMR analysis showed that the product was a mixture of 95% L1.2H$_2$O and 5% Mg(OH)$_2$.

Thus, the PXRD pattern of the solid mixture showed an overlap of the patterns corresponding to L1.2H$_2$O and Mg(OH)$_2$. Extraction of this solid with methanol resulted in pure L1 (based on PXRD and $^1$H NMR spectra), and Mg(OH)$_2$ (based on PXRD). The solid mixture of L1.2H$_2$O and Mg(OH)$_2$ could be recycled by adding it to a fresh solution of the simulant, thereby initiating another separation cycle.

The recovered solid L1 and magnesium hydroxide were then added to a fresh simulant solution to start another cycle. Such cycling was repeated twice more. The whole process was found to be efficient with high recovery of sulfate (99.6%, 99.4%, and 97.9%) as well as good ligand recovery (92.2%, 94.7%, and 88.9%). This established that the ligand is robust enough to survive at least three recovery cycles. Although this magnesium-based system is not applicable to the full alkaline conditions encountered in the nuclear waste, the ease of operation coupled with high efficiency and good ligand recyclability opens the door to other industrial sulfate separations from simpler, less basic aqueous solutions.

Example 7

Sulfate Separation from Complex Simulants Using Compound 2

Table 1 lists the compositions of various waste simulants employed in this study. Simulant 1 is mildly alkaline (pH 9.5), while Simulants 2-7 are highly alkaline (pH=14). All simulants contain concentrations of Na$^+$, NO$_3^-$, and SO$_4^{2-}$ comparable with those found in the nuclear waste (Moyer et al. 2008). Additionally, Simulants 3-7 contain extra anions present in significant amounts in the nuclear waste, namely NO$_2^-$, Al(OH)$_4^-$, and CO$_3^{2-}$.

TABLE 1

| Compositions of the nuclear waste simulants | | | | | | | | | |
|---|---|---|---|---|---|---|---|---|---|
| Simulant | Na$^+$ | SO$_4^{2-}$ | OH$^-$ | NO$_3^-$ | NO$_2^-$ | Al(OH)$_4^-$ | CO$_3^{2-}$ | pH | cation |
| 1 | 6.04 | 0.0440 | 0.05 | 5.9 | — | — | — | 9.5 | Mg |
| 2 | 6.00 | 0.0322 | 1.45 | 4.49 | — | — | — | 14 | Na |
| 3 | 6.00 | 0.0322 | 1.45 | 3.32 | 1.17 | — | — | 14 | Na |
| 4 | 6.00 | 0.0322 | 1.45 | 2.75 | 1.17 | 0.57 | — | 14 | Na |
| 5 | 6.00 | 0.1190 | 0.96 | 3.57 | 0.92 | 0.31 | — | 14 | Na |
| 6 | 6.80 | 0.1190 | 0.96 | 4.37 | 0.92 | 0.31 | — | 14 | Na |
| 7 | 7.00 | 0.1190 | 0.96 | 3.84 | 0.92 | 0.31 | 0.37 | 14 | Na |

Concentrations of the ionic components in mol/L.

Selective crystallization of the sodium-based system was further explored for sulfate separation from solutions that more realistically simulate nuclear waste from the Hanford nuclear waste (Simulants 2-7). Two equivalents of solid L1.2H$_2$O was added per equivalent of sulfate ion in the simulant solution and stirred in a vortexer at room temperature for 4 days. All crystallized solids were analyzed by PXRD and FTIR spectroscopy. Additionally, the amount of crystallized sulfate was analyzed gravimetrically by dissolution of the isolated solids in dilute nitric acid and precipitation with Ba$^{2+}$.

Figure 6:
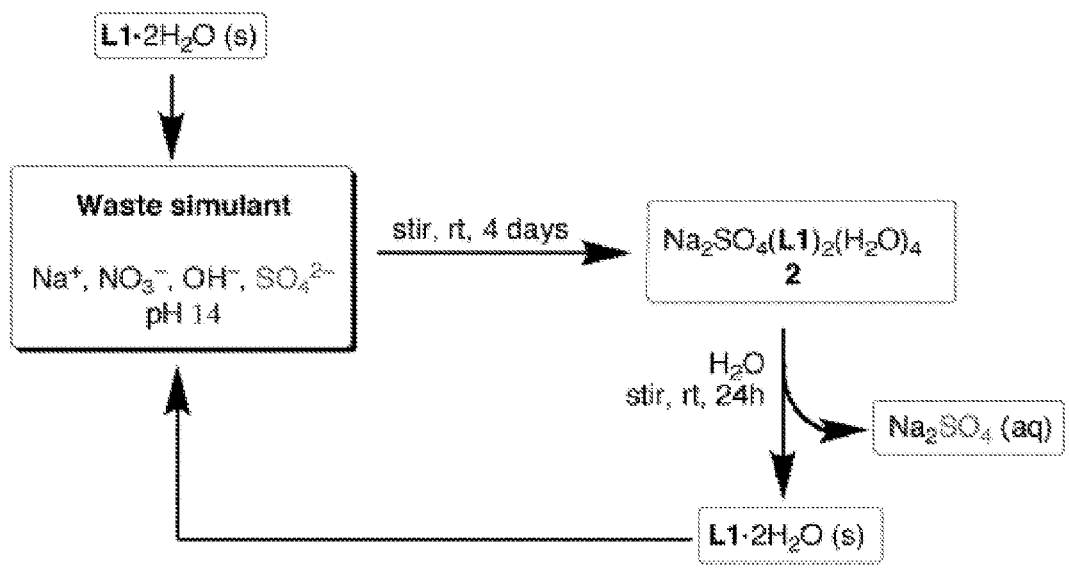
FIG. 6 illustrates a sulfate separation cycle involving crystallization of Compound 1 with L1 and recovery/reuse of L1.

The results in Example 4 indicated that sulfate can be selectively separated in 90% yield by crystallization of Compound 1 from highly alkaline (pH 14) sodium nitrate solutions, and the ligand L1 can be easily recovered in almost quantitative yield by recrystallization from fresh water, releasing the sodium sulfate for disposal (FIG. 6).

These results were confirmed using a similar alkaline sodium nitrate solution (Simulant 2), from which sulfate could be separated in 84% as crystalline Compound 1. The effect of other major competing anions in the waste (i.e., $NO_2^-$, $Al(OH)_4^-$, $CO_3^{2-}$) on the crystallization efficiency of Compound 1 was examined by gradually increasing the complexity of the simulant solutions.

Figure 7:
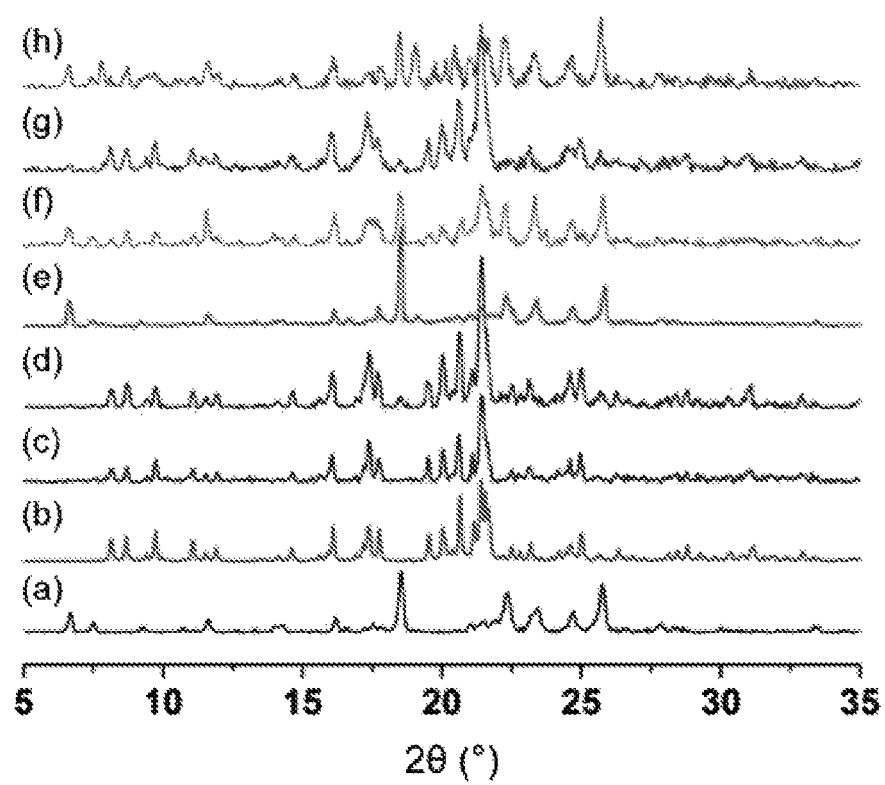
FIG. 7 shows the PRXD patterns of sulfate separation by crystallization of Compound 1 obtained in Example 7. The patterns are (a) experimental pattern of L1.$2H_2O$; (b) simulated pattern from the single-crystal X-ray data of Compound 1; (c) experimental pattern of Compound 1 crystallized from Simulant 2; (d) experimental pattern of Compound 1 crystallized from Simulant 3; (e) experimental pattern of Compound 1 crystallized from Simulant 4; (f) experimental pattern of Compound 1 crystallized from Simulant 5; (g) experimental pattern of Compound 1 crystallized from Simulant 6; (h) experimental pattern of Compound 1 crystallized from Simulant 7. The simulant compositions are provided in Table 1.

The presence of nitrite (1.17 M), the next most abundant anion in the waste after $NO_3^-$ and $OH^-$, had virtually no effect on the crystallization of Compound 1, which was isolated in 86% from Simulant 3. The presence of 0.57 M aluminate in Simulant 4 completely inhibited the crystallization of Compound 1, and only unreacted L1.2H$_2$O was isolated. However, when a different Hanford simulant composition (Moyer et al. 2008) was employed, containing a lower concentration of 0.31 M aluminate (Simulant 5), a mixture of Compound 1 and L1.2H$_2$O crystallized, as indicated by PXRD analysis (FIG. 7). Increasing the amount of nitrate (Simulant 6) led to almost exclusive crystallization of Compound 1, with only traces of L1.2H$_2$O detected by PXRD. The sulfate separation yield from this simulant solution was 72%. Finally, Simulant 7, containing a mixture of all the major anions present in the Hanford tanks, was employed in a final test for sulfate separation efficacy from realistic waste compositions. Under these conditions, a mixture of crystalline Compound 1 and L1.2H$_2$O was isolated, and the observed sulfate separation yield was 41%. Given that L1 can be easily recovered in excellent yield by simple recrystallization from water (Example 4), selective crystallization of Compound 1 appears as a viable approach to sulfate separation from the Hanford waste.

Example 8

Selectivity Trends in Competitive Crystallizations

The experiments described below were generally conducted as described above and as described in Rajbanshi et al. 2012.

Detailed structural investigation of the Na-based system indicated that the L1 capsules are a good fit for the tetrahedral $SO_4^{2-}$, $SeO_4^{2-}$ and $CrO_4^{2-}$ anions as a result of 12 complementary hydrogen bonds from the six urea groups lining the cavities. The pyramidal-shaped $SO_3^{2-}$, on the other hand, did not fit so well inside the capsules, engaging in repulsive NH.S interactions. Though the crystal structure of the Na capsule with $CO_3^{2-}$ has yet to be determined, it is likely this anion also engages in repulsive NH . . . C interactions. The capsules in the Na-based system also showed a high degree of organizational rigidity, displaying minimal structural variation with the change in the encapsulated anion. For these reasons, the capsules show good shape recognition for tetrahedral oxoanions in the crystalline state.

Pairwise competitive crystallization experiments with L1 (two equivalents), one equivalent of Na$_2$SO$_4$ and one equivalent of Na$_2$SO$_3$ or Na$_2$CO$_3$ in H$_2$O/MeOH solutions resulted in formation of crystals containing $SO_4^{2-}$ as the major anion. The elemental analysis of the same crystalline solids showed the anion selectivity to follow the order $SO_4^{2-}>SO_3^{2-}>CO_3^{2-}$ with observed molar ratios of sulphate over the competing sulphite and carbonate anions of 5.9 and 11.5, respectively.

To assess the size recognition of the crystalline capsule in the Na-based system, similar pairwise competitive crystallization experiments were performed with L1 (two equivalents) and Na$_2$SO$_4$/Na$_2$SeO$_4$ mixtures (one equivalent each) in H$_2$O/MeOH. The $SO_4^{2-}$ versus $SeO_4^{2-}$ competition is ideal for probing the size selectivity, as these two anions have the same tetrahedral shape, very similar basicities (pKa=1.99 and 1.70 for $HSO_4^{2-}$ and $HSeO_4^{2-}$, respectively), but slightly different sizes ($d_{S-O}$=1.49 Å, $d_{Se-O}$=1.65 Å). The $SO_4^{2-}$/$SeO_4^{2-}$ molar ratio found in the crystalline solid resulting from the competitive crystallization was 31.3, indicating strong size recognition for $SO_4^{2-}$. The observed sulphate preference in Na-based system is much more pronounced than in the Mg system (Rajbanshi et al. 2012), which displayed a corresponding $SO_4^{2-}$/$SeO_4^{2-}$ ratio of only 3. The increased $SO_4^{2-}$/$SeO_4^{2-}$ selectivity in the Na-based system may be attributed to the smaller size of the Na capsule (d(N . . . N)=9.51 Å) compared to the Mg capsule (d(N . . . N)=9.65 Å), which favored the smaller sulphate anion.

In comparison with the good $SO_4^{2-}$/$SeO_4^{2-}$ selectivity observed in the Na-based crystallizations, the competitive crystallization experiment involving a Na$_2$SO$_4$/Na$_2$CrO$_4$ mixture under similar conditions yielded crystals with a $SO_4^{2-}$/$CrO_4^{2-}$ ratio of only 2.0. While chromate has a size almost identical to selenate ($d_{Cr-O}$=1.64 Å), $CrO_4^{2-}$ has a higher basicity (pKa=6.51 for $HCrO_4^{2-}$). As a result, binding of chromate is inherently favored due to its stronger hydrogen bond acceptor ability compared to sulphate, a factor that apparently offsets much of the size discrimination effect.

For the K-based system, pairwise competitive crystallizations with L1 gave $SO_4^{2}$/$SeO_4^{2-}$ selectivity and $SO4^{2-}$/$CrO_4^{2-}$ selectivity ratios of 13.3 and 1.1, respectively. The potassium capsule was the smallest of the three systems (d(N . . . N)=9.21 Å).

REFERENCES

Ballester, P. (2010) *Chem. Soc. Rev.*, 39, 3810-3830.
Belcher, R.; Gibbons, D. (1952) *J. Chem. Soc.*, 4216-4118.
Benatti, C. T.; Tavares, C. R. G.; Lenzi, E. (2009) *J. Environ. Management*, 90,504-511.
Berrocal, M. J.; Cruz, A.; Badr, I. H. A.; Bachas, L. G. (2000) *Anal. Chem.*, 72, 5295.
Boari, G.; Liberti, L.; Santori, M.; Spinosa, L. (1976) *Desalination*, 19,283-298.
Boukhalfa, C.; Mennour, A.; Reinert, L.; Fuzellier, H. (2007) *Desalination*, 214,38-48.
Bunker, B.; Virden, J.; Kuhn, B.; Quinn, R. (1995) *Encyclopedia of Energy Technology and the Environment*; John Wiley & Sons, Inc., pp 2023-2032.
Byrne, P.; Turner, D. R.; Lloyd, G. O.; Clarke, N.; Steed, J. W. (2008) *Cryst. Growth. Des.*, 8, 3335-3344.
Custelcean, R. (2010a) *Chem. Soc. Rev.*, 39, 3675-3685.
Custelcean, R. (2009a) *Curr. Opin. Solid State Mater. Sci.*, 13, 68.
Custelcean, R.; Bock, A.; Moyer, B. A. (2010b) *J. Am. Chem. Soc.*, 132, 7177-7185.
Custelcean, R.; Moyer, B. A. (2007) *Eur. J. Inorg. Chem.*, 1321.
Custelcean, R.; Moyer, B. A.; Bryantsev, V. S.; Hay, B. P. (2006) *Cryst. Growth. Des.*, 6, 555-563.
Custelcean, R.; Moyer, B. A.; Hay, B. P. (2005) *Chem. Commun.*, 5971-5973.
Custelcean, R.; Remy, P. (2009b) *Cryst. Growth. Des.*, 9, 1985-1989.
Custelcean, R.; Remy, P.; Bonnesen, P. V.; Jiang, D. E.; Moyer, B. A. (2008) *Angew. Chem. Int. Ed.*, 47, 1866-1870.
Darbi, A.; Viraraghavan, T.; Jin, Y. C.; Braul, L.; Corkal, D. (2003) *Water Qual. Res. J Can.*, 38,169-182.
Delmau, L. H.; Birdwell Jr., J. F.; McFarlane, J.; Moyer, B. A. (2010) *Solvent Extr. Ion Exch.*, 28, 19-48.
Haghsheno, R.; Mohebbi, A.; Hashemipour, H.; Sarrafi, A. (2009) *J. Haz. Mater.*, 166,961-966.
Hay, B. P.; Firman, T. K.; Moyer, B. A. (2005) *J. Am. Chem. Soc.*, 127, 1810.

Hay, M.; Coleman, C.; Hassan, N.; McCabe, D.; King, B.; Nash, C.; Saito, H.; Calloway, B.; Crawford, C. (2001) *WSRC-TR*-2000-00489, Westinghouse Savannah River Company: Aiken, S.C.

Jong, T.; Parry, D. L. (2003) *Water Res.*, 37,3379-3389.

Kang, S. O.; Llinares, J. M.; Day, V. W.; Bowman-James, K. (2010) *Chem. Soc. Rev.*, 39, 3980-4003.

Lumetta, G. J. (2004) *The Problem with Anions in the DOE Complex, in Fundamentals and Applications of Anion Separations*; Moyer, B. A., Singh, R. P., Eds.; Kluwer Academic: New York, pp 107-114.

Malaiyandi, M.; Sastri, V. S. (1981) *Sep. Sci. Technol.*, 16,371-376.

Manara, D.; Grandjean, A.; Pinet, O.; Dussossoy, J. L.; Neuville, D. R. (2007) *J. Non-Cryst. Solids*, 353,12-23.

Moyer, B. A.; Birdwell Jr., J. F.; Delmau, L. H.; McFarlane, J. (2008) *ORNL/TM*-2008-073, Oak Ridge National Laboratory: Oak Ridge, Tenn.

Moyer, B. A.; Delmau, L. H.; Fowler, C. J.; Ruas, A.; Bostick, D. A.; Sessler, J. L.; Katayev, E.; Pantos, G. D.; Llinares, J. M.; Hossain, M. A.; Kang, S. O.; Bowman-James, K. (2006) *Supramolecular Chemistry of Environmentally Relevant Anions, in Advances in Inorganic Chemistry*; van Eldik, R., Bowman-James, K., Eds.; Elsevier: Oxford, Vol 59, pp 175-204.

Pflugrath, J. W.; Quiocho, F. A. (1985) *Nature*, 314, 257-260.

Priyantha, N.; Perera, S. (2000) *Water Res. Manage.*, 14,417-433.

Rajbanshi, A.; Custelcean, R. (2012) *Supramolecular Chem.*, 24, 65.

Rajbanshi, A.; Moyer, B. A.; Custelcean, R. (2011) *Cryst. Growth. Des.*, 11, 2702-2706.

Raposo, C.; Almaraz, M.; Martín, M.; Weinrich, V.; Mussóns, M. L.; Alcázar, V.; Caballero, M. C.; Morán, J. R. (1995) *Chem. Lett.*, 759.

Ravikumar, I.; Ghosh, P. (2012) *Chem. Soc. Rev.*, 41: 3077-3098.

Tait, S.; Clarke, W. P.; Keller, J.; Batstone, D. J. (2009) *Water Res.*, 43,762-772.

Wang, K. Y.; Chung, T. S.; Rajagopalan, R. (2007) *Ind. Eng. Chem. Res.*, 46,1572-1577.

Wilmarth, W. R.; Lumetta, G. J.; Johnson, M. E.; Poirier, M. R.; Thompson, M. C.; Suggs, P. C.; Machara, N. P. (2011) *Solvent Extr. Ion Exch.*, 29, 1-49.

Wu, B.; Liang, J.; Yang, J.; Jia, C.; Yang, X-J.; Zhang, H.; Tang, N.; Janiak, C. (2008) *Chem. Commun.*, 1762-1764.

We claim:

1. A method for selective anion separation which comprises
(a) admixing (N-[2-[bis[2-[N'(3-pyridyl)ureido]ethyl]-N-amino]ethyl]-N'-(3-pyridyl)urea) ("L1") with an aqueous, alkaline solution, the aqueous alkaline solution comprises at least a stoichiometric amount of $Na^+$ or $K^+$ ions, or both, and of a tetrahedral divalent oxoanion ("oxoanion") and of competitive anions, said aqueous alkaline solution lacks divalent metal cations, for a time of at least 1 day to form a crystalline solid of $Na_2$(oxoanion)$(L1)_2(H_2O)_4$ or of $K_2$(oxoanion)$(L1)_2(H_2O)_2$, or of both; and
(b) separating said crystalline solid from said solution.

2. The method of claim 1, wherein said tetrahedral, divalent oxoanion is selected from the group consisting of sulfate, selenate, chromate, tellurate, molybdate and tungstate.

3. The method of claim 1, wherein said solution comprises about 3, 4, 5 or 6 M Na+ ions.

4. The method of claim 1, wherein said solution has a pH ranging from greater than about 9.5 to about 14.

5. The method of claim 1, wherein L1 is added as a solid.

6. The method of claim 1, wherein two equivalents of L1 are added per equivalent of oxoanion.

7. The method of claim 1, which further comprises (c) recovering Li from said crystalline solid.

8. The method of claim 1, wherein said aqueous alkaline solution is nuclear waste.

9. The method of claim 8, wherein said tetrahedral divalent oxoanion is a sulfate anion.

10. The method of claim 1, wherein said aqueous alkaline solution is Bayer liquor.

11. The method of claim 10, wherein said tetrahedral divalent oxoanion is sulfate or chromate.

12. A method of selective anion separation which comprises
(a) admixing (N-[2-[bis[2-[N'-(3-pyridyl)ureido]ethyl]-amino]ethyl]-N'-(3-pyridyl)urea) ("L1") with an aqueous neutral or alkaline solution lacking divalent metal cations, the aqueous neutral or alkaline solution comprises at least a stoichiometric amount of Na+ or K+ ions, or both, and of a tetrahedral divalent oxoanion ("oxoanion") and of competitive anions, for a time of at least 1 day to form a crystalline solid comprising $Na_2$(oxoanion)$(L1)_2(H_2O)_4$ or of $K_2$(oxoanion)$(L1)_2(H_2O)_2$, or of both; and
(b) separating the crystalline solid from the remaining solution.

13. The method of claim 12, wherein said tetrahedral, divalent oxoanion is selected from the group consisting of sulfate, selenate, chromate, tellurate, molybdate, and tungstate.

14. The method of claim 12, wherein said solution comprises about 3, 4, 5 or 6 M Na* ions.

15. The method of claim 12, wherein L1 is added as a solid.

16. The method of claim 12, wherein two equivalents of L1 are added per equivalent of oxoanion.

17. The method of claim 12, which further comprises (c) recovering L1 from said crystalline solid.

18. A method of sulfate separation from nuclear waste which comprises
a) admixing (N-[2-[bis[2-[N'-(3-pyridyl)ureido]ethyl]-amino]ethyl]-N'-(3-pyridyl)urea) ("L1") with a nuclear waste solution, said nuclear waste solution lacks divalent metal cations, for a time of at least 1 day to form a crystalline solid of $Na_2(SO_4)(L1)_2(H_2O)_4$; and
(b) separating said crystalline solid from said nuclear waste solution.

19. The method of claim 18, which further comprises (c) recovering L1 from said crystalline solid.

20. The method of claim 18, wherein two equivalents of L1 are added per equivalent of sulfate.

21. The method of claim 1, 12 or 18 which further comprises repeating steps (a) and (b) using recovered or fresh L1.

22. The method of claim 7, 17 or 19, wherein L1 is recovered by recrystallization from water.

23. A composition comprising a complex represented by the formula $Na_2$(anion)$(L1)_2(H_2O)_4$ or $K_2$(anion)$(L1)_2(H_2O)_2$, wherein anion is a tetrahedral divalent oxoanion, and L1 is (N-[2-[bis[2-[N'-(3-pyridyl)ureido]ethyl]-amino]ethyl]-N'-(3-pyridyl)urea), wherein said composition lacks divalent metal cations.

24. The composition of claim 23, wherein said tetrahedral, divalent oxoanion is selected from the group consisting of sulfate, selenate, chromate, tellurate, molybdate and tungstate.

25. The composition of claim 23, wherein said complex is $Na_2SO_4(L1)_2(H_2O)_4$ or $K_2SO_4(L1)_2(H_2O)_2$.

26. The composition of claim 23, wherein said tetrahedral divalent oxoanion is sulfate anion.

* * * * *